United States Patent
Lofqvist et al.

(10) Patent No.: US 7,202,434 B2
(45) Date of Patent: Apr. 10, 2007

(54) METHOD OF SORTING OBJECTS COMPRISING ORGANIC MATERIALS

(75) Inventors: Bo Lofqvist, Lund (SE); Jesper Pram Nielsen, Hilleröd (DK)

(73) Assignee: Bomill AB, Lund (SE)

( * ) Notice: Subject to any disclaimer, the term of this patent is extended or adjusted under 35 U.S.C. 154(b) by 0 days.

(21) Appl. No.: 10/481,149

(22) PCT Filed: Jul. 3, 2002

(86) PCT No.: PCT/SE02/01335

§ 371 (c)(1),
(2), (4) Date: Jun. 28, 2004

(87) PCT Pub. No.: WO03/004179

PCT Pub. Date: Jan. 16, 2003

(65) Prior Publication Data

US 2004/0251177 A1    Dec. 16, 2004

(30) Foreign Application Priority Data

Jul. 4, 2001    (SE)    .................................... 0102395

(51) Int. Cl.
*B07C 5/00*    (2006.01)
(52) U.S. Cl. ...................... 209/576; 209/577; 209/580; 703/12
(58) Field of Classification Search ................ 209/576, 209/580
See application file for complete search history.

(56) References Cited

U.S. PATENT DOCUMENTS

| | | | |
|---|---|---|---|
| 4,203,522 A | * | 5/1980 | Fraenkel et al. ............ 209/558 |
| 4,421,772 A | | 12/1983 | Munck et al. |
| 4,535,248 A | | 8/1985 | Schade et al. |
| 4,863,041 A | | 9/1989 | Bailey |
| 4,866,283 A | | 9/1989 | Hill, Jr. |
| 5,379,764 A | * | 1/1995 | Barnes et al. ............... 600/473 |
| 6,410,872 B2 | * | 6/2002 | Campbell et al. ........... 209/577 |
| 6,871,169 B1 | * | 3/2005 | Hazen et al. .................. 703/2 |

FOREIGN PATENT DOCUMENTS

| | | |
|---|---|---|
| GB | 993063 | 5/1965 |
| GB | 2 060 166 A | 4/1981 |
| GB | 2 091 416 A | 7/1985 |

* cited by examiner

*Primary Examiner*—Gene O Crawford
*Assistant Examiner*—Terrell Matthews
(74) *Attorney, Agent, or Firm*—Merchant & Gould P.C.

(57) ABSTRACT

A method of sorting sorting objects within a bulk of objects from a heterogeneous population is provided. The bulk of objects to be sorted has an inherent variation, and at least one class, having less variation than the originally inherent variation of the bulk, is separated from the bulk. This lesser variation represents a quality of composition with reference to any organic material of the objects within the bulk. The method comprises the steps of distributing each of the objects to be separated as a separate object in a sorting device; exposing the separate object to energy emitted from at least one energy source; recording from at least one point of the separate object by means of at least one sensor a first multivariate signal; predicting or classifying, by means of a calibration method previously performed on a subset of the population, between the first multivariate signal and the quality of composition, a second signal expressing the magnitude of at least one quality variable of univariate variation; and separating the separate object from the sorting device to the at least one collected class in dependence on the magnitude of the at least one quality variable of the second signal from the at least one point.

26 Claims, 6 Drawing Sheets

METHOD OF SORTING OBJECTS COMPRISING ORGANIC MATERIALS

This application is a 371 of PCT/SE02/01335 filed on Jul. 3, 2002,which claims benefit of SE 0102395-1, filed on Jul. 4, 2001.

The invention refers to a method of sorting objects. More specifically, the invention refers to a method of sorting objects within a bulk of objects from a heterogeneous population by separating from a sorting device at least one collected class of different quality of composition with reference to any organic material of the objects.

There exist a number of methods for sorting objects according to outer attributes, such as length, size and density.

For example, in the cleaning of grains it is common to use machines designed to screen out impurities, such as over- and undersized material, or to classify grains, for example malting barley, according to the width of the kernels. Further gravity tables are used to sort granular materials according to the density of the granules.

There are also cleaning machines for granular materials, which remove impurities according to their colour. In these machines the material to be cleaned is made to fall into the free atmosphere, ideally one by one. During their fall the objects are illuminated with light. The reflected, transmitted, or emitted light from each object is detected at 1–3 pre-selected bands of wavelength in the visible and/or infrared (IR) regions by use of optical filters. These bands are pre-selected in order to give a signal corresponding to a known sorting characteristic of the objects to be removed, for example discolouration. Furthermore, in these methods the optical filters are selected so that there is a substantial difference in the transmitted, reflected, or emitted light between a wanted or unwanted object.

An optical sorting apparatus for agricultural products is shown in U.S. Pat. No. 4,863,041, which has a background device for comparison of the colour and/or the brightness of the object to be sorted. The background device is dynamically variable in order to provide an adjustable reference for an optical detector. Objects to be cleaned are similarly positioned in front of a suitable background in GB 2 091 415 as well as in U.S. Pat. No. 4,203,522.

In U.S. Pat. No. 4,421,772 a method for identifying botanical components parts of ground seeds is shown, wherein a lighting system for fluorescent microscope is used. Fluorescence is also utilized in U.S. Pat. No. 4,866,283 for the inspection and cleaning of beans, nuts, and pulses, for example peanuts, where laser-induced luminescence is used to detect impurities. The inspection system comprises an excitation means for illuminating an object to cause it to produce fluorescent radiation. A specific characteristic reading produced by the object is compared to a reference reading in order to obtain an indication of one specific characteristic of the object. In this way, the system identifies and removes undesired or damaged objects, e.g. peanuts contaminated with aflatoxin, from a stream of objects by determining fluorescence at a predetermined wavelength.

The detection of aflatoxin by means of fluorescence after exposure to long-wave ultraviolet radiation has also been accomplished in U.S. Pat. No. 4,535,248.

In GB 2 060 166 differences between two materials are distinguished by utilizing a device with two filters. In this device a mixture of two different materials are fed through a testing zone into which light pulses with two alternating frequencies are directed. These two frequencies correspond to the characteristic frequencies of the amplitude peaks for the light reflected by each material, the reflected light pulses being evaluated to provide a rejection signal for the physical separation of the two materials when a reflected pulse has a specific relationship.

There is no indication in the prior art methods that a multivariate calibration, which describes the heterogenity of composition of the objects to be sorted, should be performed before the actual sorting.

In such traditional methods the reflected, transmitted, or emitted light is registered. Three wave-lengths at the most are analyzed, one within the visible light region and two within the IR region. Thus, a feature of the object is determined with reference to the recording from one to three wave-lengths only.

Furthermore, simultaneous measurements of several (>3) wavelengths can not be performed with such a filter arrangement while assuming that the light hitting each filter will be reflected from one and the same well-defined point on an object and/or with one and the same angle.

Neither is the removal of an object in a colour sorter specific, since the air jet ejector used also removes from their falling line several objects in the vicinity of that object which is to be removed. Thus, the purity of the removed fraction is low and it contains—at the best—2–3 times as many non-selected objects as the number of objects selected for removal.

Furthermore, the objects in the vicinity of those removed are influenced and brought out of their falling line and their positions can thus not be identified. This means that the sorting of any of these objects is even more inaccurate and limits the application of colour sorters to cleaning tasks, where the percentage of impurities is low.

An inherent property in a population of objects of biological origin as well as many man-made objects comprising organic material is that they exhibit a variation in one or several different qualities of composition. Such an inherent variation or heterogenity is, in contrast to impurities, an integrated property of a population. Thus, there exist several types of qualities or properties, which can not be determined by one, two or three wave-lengths.

The purpose of the invention is to achieve a method of sorting objects whereby the above-mentioned problems are eliminated.

A further purpose of the invention is to provide a method, in which the total population of objects to be sorted are classified with reference to its heterogenity in one or more of its qualities of composition.

Another purpose of the invention is to provide a method which will allow the identification of intact objects of a heterogeneous population and the sorting of them into two or more classes, each being more homogeneous than the original non-sorted material.

Still another purpose of the invention is to provide a method, whereby organic materials can be measured, evaluated as well as sorted in one process into more useful and valuable classes.

Yet another purpose of the invention is to provide a method of high sorting capacity, which is suitable for sorting of bulk materials, such as raw materials or semi-manufactures for industrial production without affecting the normal production procedures of an industrial process.

In order to achieve these purposes, the present invention provides a method of sorting objects within a bulk of objects from a heterogeneous population. This bulk of objects to be sorted has an inherent variation. At least one class, having less variation than the originally inherent variation, is separated from the bulk, and this lesser variation represents a quality of composition with reference to any organic material of the objects within the bulk.

In this connection the term "organic material" pertains to substances derived from living organisms and chemical substances containing covalently bound carbon atoms as well as textures, structures etc, which are formed thereof. Of course, the inventive method can also be used for classifying and sorting inorganic objects.

The inventive method comprises the steps of
(a) distributing each of said objects to be separated as a separate object in a sorting device;
(b) exposing said separate object to energy from at least one energy source;
(c) recording from at least one point of said separate object by means of at least one sensor a first multivariate signal;
(d) predicting or classifying, by means of a multivariate calibration method previously performed on a subset of said population, between said first multivariate signal and said quality of composition, a second signal expressing the magnitude of at least one quality variable of univariate variation; and
(e) separating said separate object from said sorting device to said at least one collected class in dependence on the magnitude of at least one quality variable of said second signal from said at least one point.

The present invention provides a new concept of sorting by exploiting the inherent heterogenous nature of organic materials of for example biological origin. The invention is based on the observation that objects comprising organic material often exhibit a large variation in their absorption of electromagnetic radiation in general at a large number of specific energies. For example, a large number of single granules in granular materials have been analyzed by using new analytical techniques. The inventors have surprisingly found that a huge variation from granule to granule in such materials can be utilized for sorting into more homogenous classes. This inherent variation is, of course, not obtained as a colour difference in the material, which indicates impurities, or as a difference, which can be attributed to a variation in intensity of reflected, transmitted, or emitted light at 1–3 fixed wave-lengths.

Such a multivariate variation reflects an inherent variation in known and/or unknown parameters of quality, which characterises each object. These parameters of quality can not be related directly to the readings registered according to the state of the art.

A simultaneous measurement of for example transmitted, reflected, and/or emitted electromagnetic radiation in general is accomplished at a large number of energies in one or more selected regions of radiation so that a spectrum can be recorded for each object. The variation in intensity at different wavelengths between the different spectra is used to sort the objects. The different levels of the reflected, transmitted, or emitted radiation then correspond to different variables. The large number of intensity values at different levels of energy in each spectrum is further processed for each object into one signal only, which is used for sorting the objects into different classes. Thus, typically a large number of different values, at least four singular intensity values, are reduced into a signal for sorting the objects. The technique is used to sort objects so that the inherent variation between objects in a class is reduced and/or minimized. This lesser inherent variation can for example be achieved by reducing the large number of absorption values recorded at the different levels of energy into a few quality variables, which parameters describe the inherent variation in the material to be sorted. These quality variables are chosen in such a way that they describe as high a portion as possible or a specific portion of the variation in the spectra of a set of reference objects.

More specifically, the inventive method is designed to sort by means of a sorting device objects within a heterogeneous population into at least two collected classes of different qualities of composition with reference to any organic material of the objects. At least one collected class exhibits less variation than the original non-sorted population.

In this connection a quality of composition is a peculiar, distinct, or essential character, which can be defined or which remains undefined. Thus, the heterogeneity can be unknown with reference to its nature, i.e. not yet ascribed to a single or a combination of two or more quality parameters. In contrast to the state of the art, in which one occasional undesired object of a population is removed, the present invention utilizes integrated heterogenities in qualities of composition of a population for sorting.

A quality of composition, as used in the present invention, can be a variation in chemical composition from object to object, i.e. a variation in quality as well as quantity. However, it can as well be a derived property like wetability, flavour, thermal plasticity, millability, or a potential of a certain class of the objects to cause good baking quality of a seed after processing, a large volume of popcorn after popping, a particular strength of a plastic object, pharmaceutical pills having no tendency to burst, a less bitter taste of chocolate after processing of cocoa beans, etc. Thus, the quality of composition can be a chemical quality, a structural quality, a sensoric quality, or a functional quality. Of course, these qualities of composition can be combined, since for example a good baking quality can only be partly derived from the protein content.

Every mechanical system can be used as a sorting device in connection with the inventive method, which is designed for arranging objects in such a way that they, in contrast to the above-mentioned colour sorter, can be systematically organized according to specified instructions and removed from their positions with high precision without influencing adjacent objects.

Each of the objects to be separated is according to the invention first distributed as a separate object in a sorting device. Then each of the separate objects is exposed to energy emitted from at least one energy source. The energy emitted can be electromagnetic radiation and/or sonic waves.

Any electromagnetic radiation or sonic waves, alone or in combination, can be used, such as ultraviolet light, visual light, near infrared light, infrared light, fluorescent light, ultrasonic waves, microwaves, or nuclear magnetic resonance.

Preferably, the energy source(s) emit(s) energy which by reflection, transmission, or emission from the objects results in a response with a high selectivity in respect of heterogeneity of the material to be sorted.

In order to ensure a high sorting capacity, it is an important aspect of the inventive method that the time used for recording and analysing data can be adjusted to an optimal speed of distribution and/or rejection of particular types of objects. Thus, the recording of the first multivariate signal from any point of an object to be sorted should not be performed for a longer time period than 20–30 ms, preferably 5 ms.

A first multivariate signal is recorded from at least one point of each separate object by means of at least one sensor. The sensor can be either univariate or multivariate, i.e. constructed for measurement of one or simultaneous measurement of more than one wavelength, respectively, as singular intensities for each of four or more wavelengths or as a sum of four or more wavelengths. The recording can take place both when the separate object is stationary and when it is moving under the sensor(s). If necessary, several sensors are used so that a satisfactory correlation can be obtained to the quality of the object.

For example, if only one sensor is used, it has the capacity to register reflected and/or transmitted and/or emitted electromagnetic radiation and/or sonic waves at more than three wavelengths as singular intensities or as a sum of intensities. In the inventive method the first multivariate signal for each object is then processed into a signal for precision sorting.

Each recorded first multivariate signal reflects a variation in known or unknown parameters of quality characterizing each object. Since most qualities are complex, a multivariate approach is used to convert detected signals into sorting signals. This is accomplished by each first multivariate signal—measured from at least one point of the objects—being translated to (i.e. reduced to) a second univariate signal.

This second univariate signal is predicted or classified by means of a multivariate calibration method between the first multivariate signal and the quality of composition. The calibration, which is based on at least four variables, has previously been performed on a subset of the population and describes the heterogenity of composition of the bulk to be sorted. The second signal then expresses the magnitude of at least one quality variable of univariate variation. When the second signal expresses the magnitude of more than one variable, these variables can be solely predicted or solely classified or a combination of both classified and predicted variables.

Before this predicting or classifying step the first multivariate signal is preferably transformed by means of a supervised or an unsupervised pretreatment.

When the quality of composition is a defined quality of composition, the multivariate calibration is carried out by use of a supervised multivariate method. In this mathematical processing of the first multivariate signal, the quality of composition of a number of objects should be known. The first multivariate signal is decomposed in order to explain the quality of composition of a population and a regression model is established, for example by means of Partial Least Squares regression. The quality of composition can be used to supervise the algorithm in finding the relevant information in the first multivariate signal. This model is then applied on new acquired first multivariate signals of new objects to be sorted, and the quality of composition in question is predicted. The predicted magnitude of the quality composition is then used for sorting.

Examples of supervised methods to be used in the method according to the invention are Partial Least Squares (PLS) Regression, Multipel Linear Regression (MLR), Principal Component Regression (PCR), Neural Network, and N-way PLS.

Figure 3:
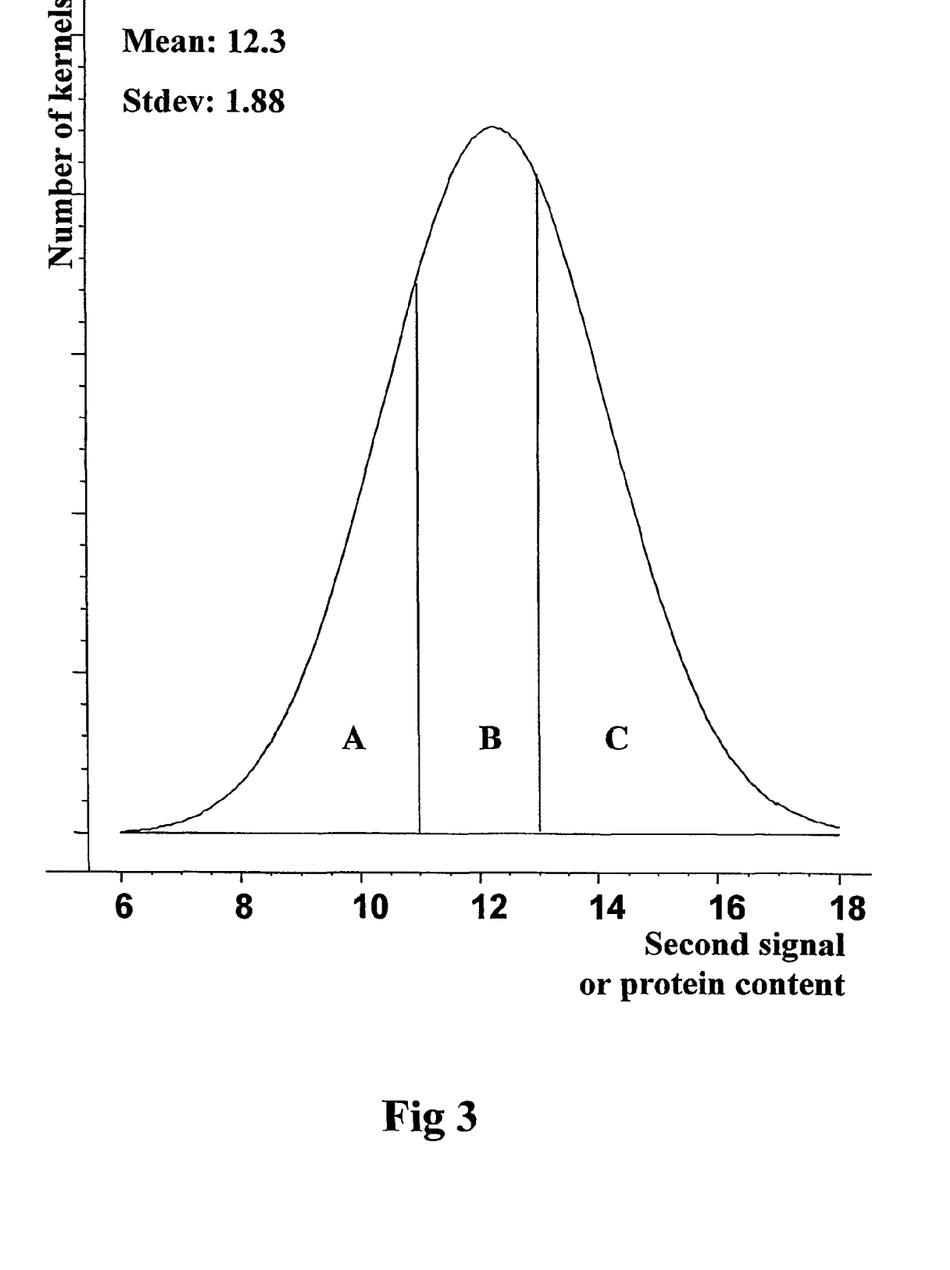
FIG. 3 shows the distribution curve of a second signal obtained for the kernels in the sample.

Thus, when the quality of composition is defined, the first multivariate signals are used directly for the prediction of a given quality parameter. The first multivariate signals (e.g. spectra)—obtained from a subset of the population—are decomposed in order to explain the quality parameter and a regression model is established, for example by PLS regression. This model is then applied on new acquired spectra as the first multivariate signals of the objects to be sorted, and the quality parameter in question is predicted. The predicted magnitude of the quality parameter is then used for sorting (c.f. FIG. 3). In this way a sorting is performed which is based on a known parameter, e.g. protein content as in FIG. 3.

When the quality of composition is of the unspecified type, i.e. undefined, the multivariate calibration is carried out by use of an unsupervised multivariate method. In this way the mathematical processing reduces the first multivariate signal to a few underlying structures. Thus, the variation in the spectra is utilized without defining the quality of composition (no supervision) and without direct linking to an analyzed or known quality of composition.

Principal Component Analysis (PCA), SIMCA, PARAFAC and TUCKER are examples of unsupervised multivariate methods which can be used in the method according to the invention.

Thus, when the quality of composition is undefined, the first multivariate signal (e.g. spectra) are analyzed by for example PCA. Latent variables are obtained, which are used as new univariate variables for sorting.

Of course, a latent variable—or a combination of several latent variables—is only used if they explain the variation within the heterogenous bulk quantity and improves the quality in a given application.

When the most probable sum of variations is explained, and when the quality is improved, this calibration model (latent variable or combination of latent variables) is applied on the first multivariate signal from the objects to be classified for sorting. In this way a sorting can be performed which is based on an unknown parameter, e.g. a third and a fourth latent variable.

However, the first multivariate signal may contain some information that is not related to the quality of composition. Thus, it is preferred to pre-treat this first multivariate signal before the calibration methods are applied, in order to construct more simple and robust calibration models. Of course, the pre-treatment must also be performed before prediction and classification.

Figure 1:
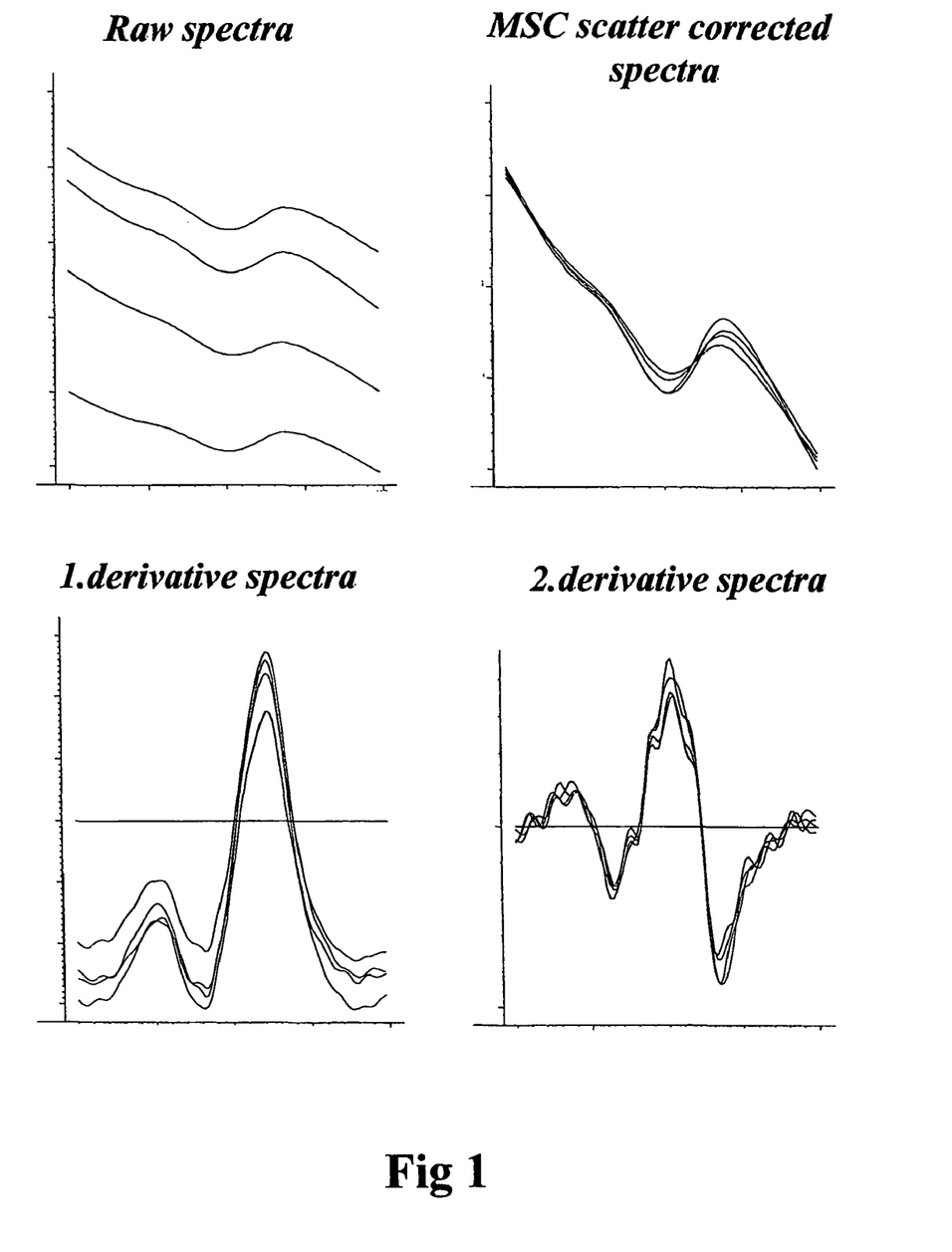
FIG. 1 shows examples of unsupervised pre-treatments performed on the first multivariate signal.

When the quality of composition is undefined, unsupervised pre-treatments are performed on the first multivariate signal. Examples of unsupervised pre-treatments are derivations, $1^{st}$ and $2^{nd}$ (or higher order) derivative, Standard Normal Variate (SNV), and Multiplicative Scatter Correction (MSC). FIG. 1 shows examples of NIT spectra in the range 850–1050 nm, represented as Raw, MSC corrected, 1.der and 2.der, respectively.

When the quality of composition is defined, supervised or unsupervised pre-treatments are performed on the first multivariate signal. The quality of composition can then be used to guide the pre-treatment in order to eliminate the irrelevant information from the first multivariate signal. Examples of supervised pre-treatments are Direct Orthogonalisation (DO) and Orthogonal Signal Correction (OSG).

EXAMPLES

The invention will now be further described and illustrated by reference to the following examples. It should be noted, however, that these examples should not be construed as limiting the invention in any way.

Example 1

Sorting of Wheat Kernels with Reference to Their Protein Content

The protein content in single wheat kernels has been found to vary substantially within a bulk sample. The baking quality for a sample of Northern European wheat has typically a variation from 8–16% between individual kernels.

Figure 2:
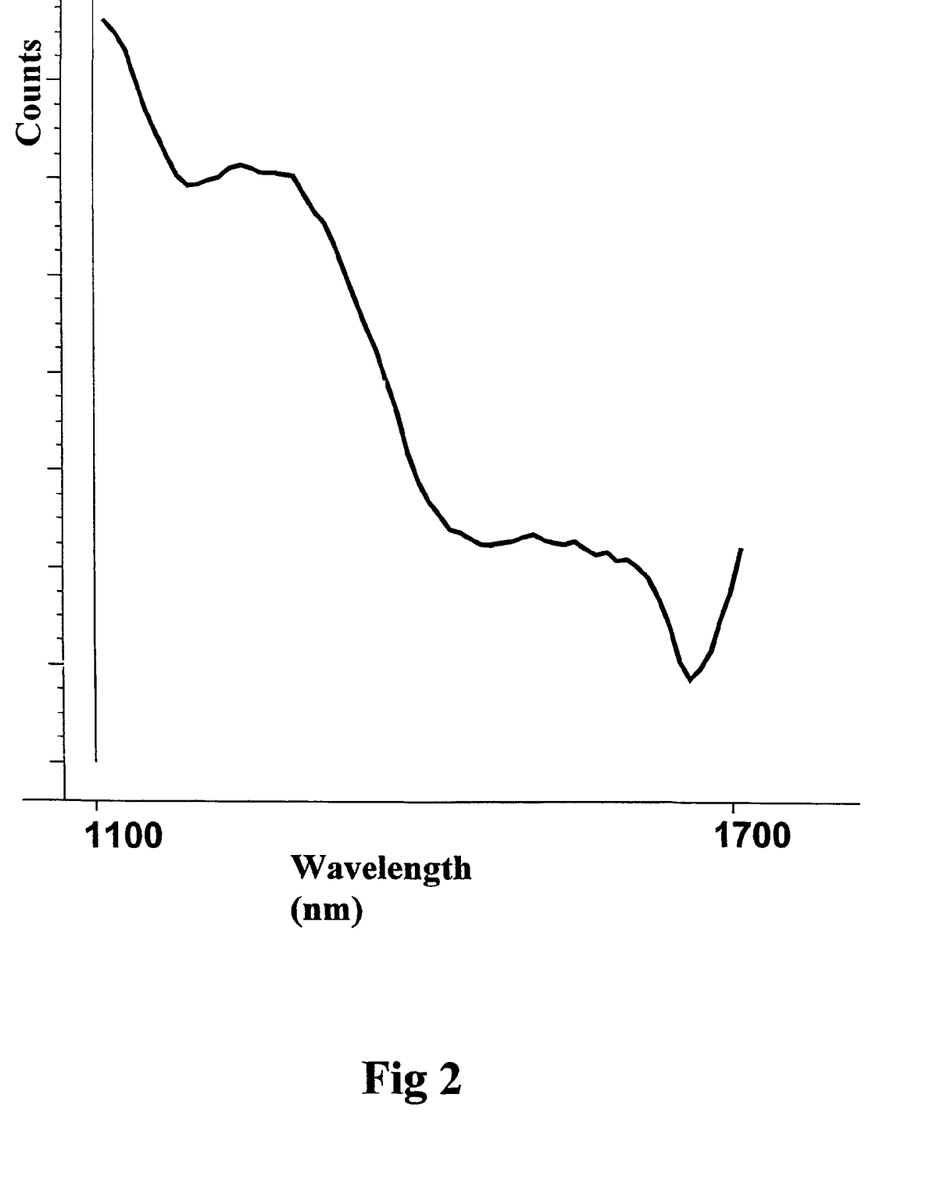
FIG. 2 shows an example of a spectrum obtained from an individual wheat kernel in a sample.

A batch of baking wheat was withdrawn from a commercial silo and sorted into three classes according the invention. The batch was fed to the distributor of the sorting device in such a way that each individual kernel obtained a fixed position and that individual kernels were fixed in such a way that they were discretely separated from each other. Each kernel in the distributor was then exposed to the light from a tungsten lamp. The light was filtered through a silicon filter with a cut-off limit at 1100 nm prior to exposure and the reflected light between 1100 and 1700 nm was recorded by use of a diode-array spectrometer. A typical example of a spectrum of a single wheat kernel spectrum from the sample is shown in FIG. 2.

A bandwidth of 10 nm is sufficient and the counts within each band were recorded. For each kernel the signals obtained from 60 bands between 1100 and 1700 nm were used as the first multivariate signal. The first multivariate signal was then pre-treated by means of the unsupervised method MSC, spectral scatter thereby being eliminated.

Prior to sorting, the protein content of a sample was determined by means of Kjeldahl analysis (AACC Method 46-12, adjusted to single seeds), and a calibration model was established between the pre-treated first multivariate signal and the protein content by using the supervised multivariate method PLSR. This model was then used to predict a second signal representing the protein content for each kernel in the sample. The distribution curve is shown in FIG. 3, the number of kernels in the batch being plotted against the second signal, which thus represents the protein content.

The batch was then sorted into three classes (A, B and C, respectively, as indicated in FIG. 3) based on the magnitude of the second signal, and the classes were collected in three separate containers. The contents were weighed and the following distribution was obtained: A:26%, B:38%, and C:36%. A sample was taken from the original non-fractionated batch and from each of the three classes obtained after sorting. These four samples were analyzed for protein by means of the Kjeldahl method, and the results are shown in Table 1 below.

TABLE 1

|  | Protein Content |
| --- | --- |
| Non-fractionated sample | 12.3% |
| Class A | 10.2% |

TABLE 1-continued

|  | Protein Content |
| --- | --- |
| Class B | 12.0% |
| Class C | 14.4% |

Thus, incoming wheat can be sorted according to the invention into two or more classes with different protein contents. These classes are suitable for different purposes, such as production of biscuit flour, cake flour, bread flour, and/or semolina for pasta.

Example 2

Sorting of Wheat Kernels According to Their Baking Quality.

It is known that different samples of wheat exhibit different baking qualities, for example in terms of loaf volume.

A sub-sample of a normal baking wheat was withdrawn from a commercial silo and fed to the distributor of the sorting device. The first multivariate signal of each individual kernel was then recorded as in Example 1. No pre-treatment of the first multivariate signals was applied and the spectra of each individual kernel were recorded.

Prior to sorting, a calibration model was established by using the unsupervised multivariate method Principal Component analysis on the first multivariate signals from the individual kernels in the sub-sample. The first two unsupervised quality variables were then combined to a second univariate signal, which was used for sorting.

Figure 4:
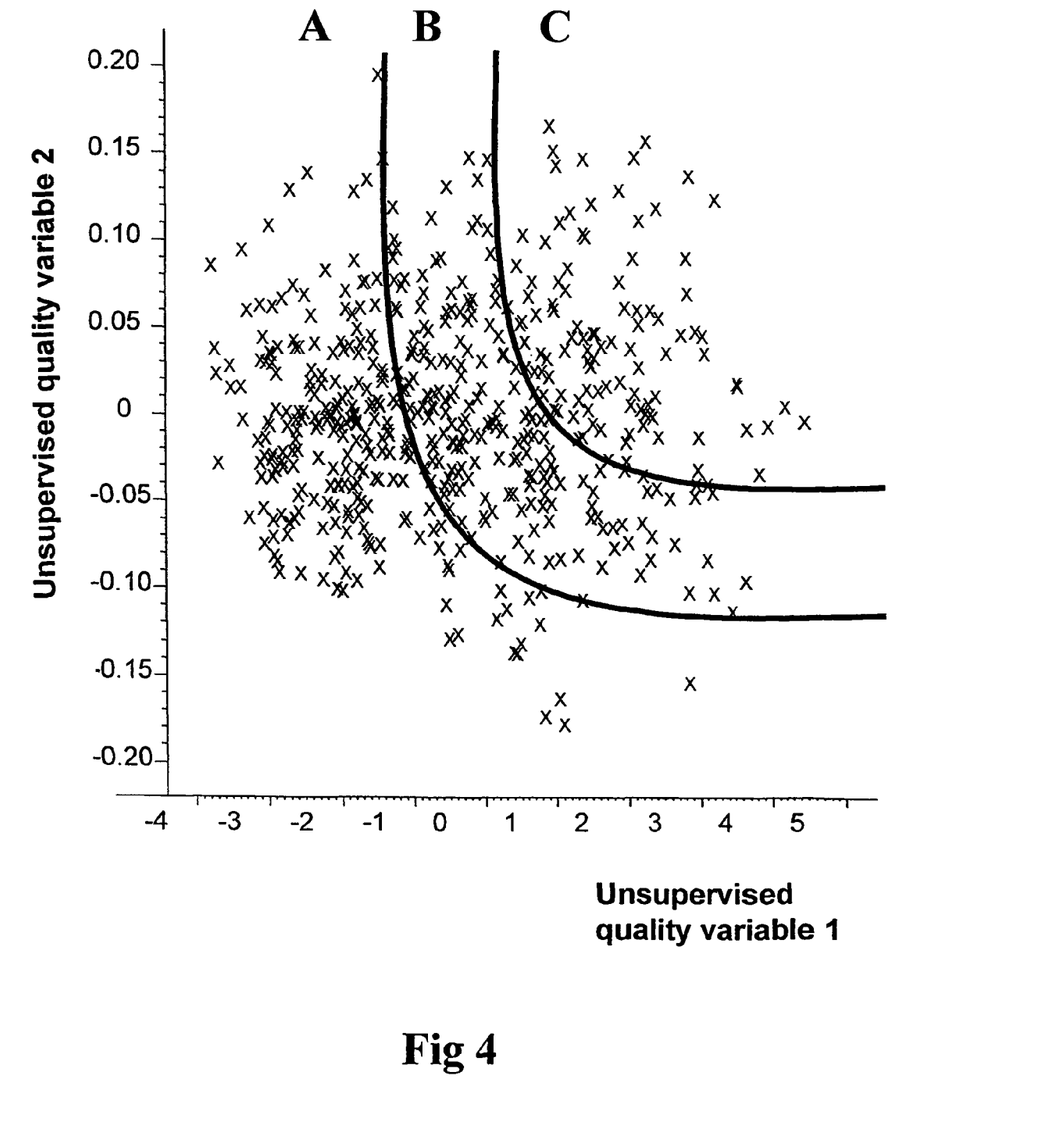
FIG. 4 shows an example of classification of a sample into three classes (A, B and C) according to a combination of two unsupervised (unknown) quality variables.

An example of classifying the kernels into three classes according to the second univariate signal is shown in FIG. 4.

The sorting device was set to separate a withdrawn batch of the normal baking wheat into three classes (A, B and C as indicated in FIG. 4) based on the magnitude of the combined second signal. The classes were collected in three separate containers.

Samples from each class were milled and tested for baking quality. It was found that the flour from class B gave the same baking results as the flour from the non-sorted batch. Flour from class C, however, resulted an increase in loaf volume of 30% after baking. The milling of class A, on the other hand, gave flour with inferior baking results in comparison with flour from class B. Furthermore, class A was found to be softer and had a lower protein content than the non-sorted batch. Such a wheat material would be more suitable for biscuit production as well as production of müsli-products or feed.

Example 3

Sorting with Reference to Popping Performance

The popping performance of popcorn is correlated to the ability of each berry to absorb energy, e.g. the microwaves in a microwave oven. The variables behind this performance are so far not fully known.

Figure 5:
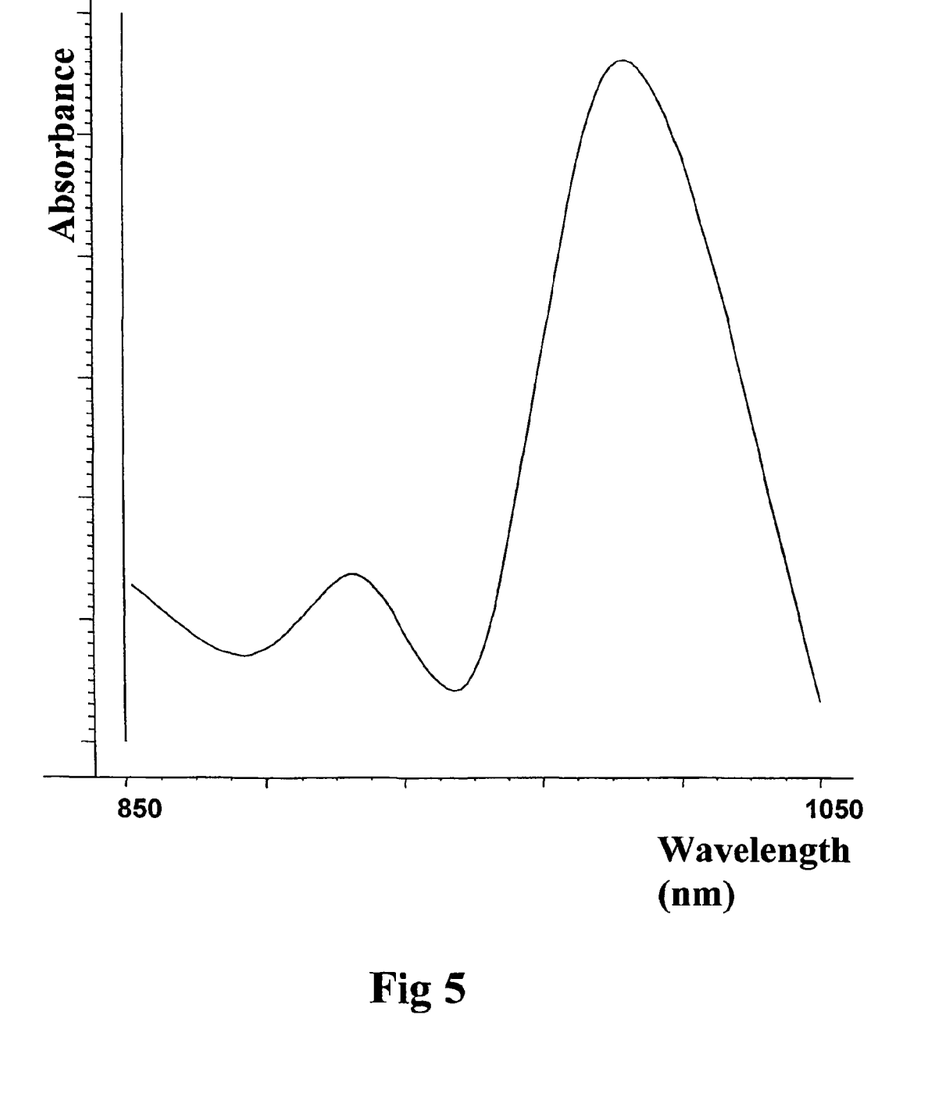
FIG. 5 shows an example of a near infrared transmittance spectrum of a popcorn berry.

A sub-sample of normal popcorn berries was fed to the sorting device. The individual berries were distributed into fixed positions as in Example 1 and then exposed to the light from a tungsten lamp. The light was chosen in such a way that the transmitted light between 850 and 1050 nm could be recorded by means of a diode array. A bandwidth of 2 nm was used, the absorbancies were recorded, and for each berry in the distributor the signal from 100 bands between 850 and 1050 nm was used as the first multivariate signal. A typical spectrum of a individual berry is shown in FIG. 5.

The first multivariate signal was pre-treated by using the unsupervised 2. derivative method. Then an unsupervised multivariate calibration model was established as in Example 2. The first unsupervised quality variable was used directly as the second univariate signal for sorting.

Figure 6:
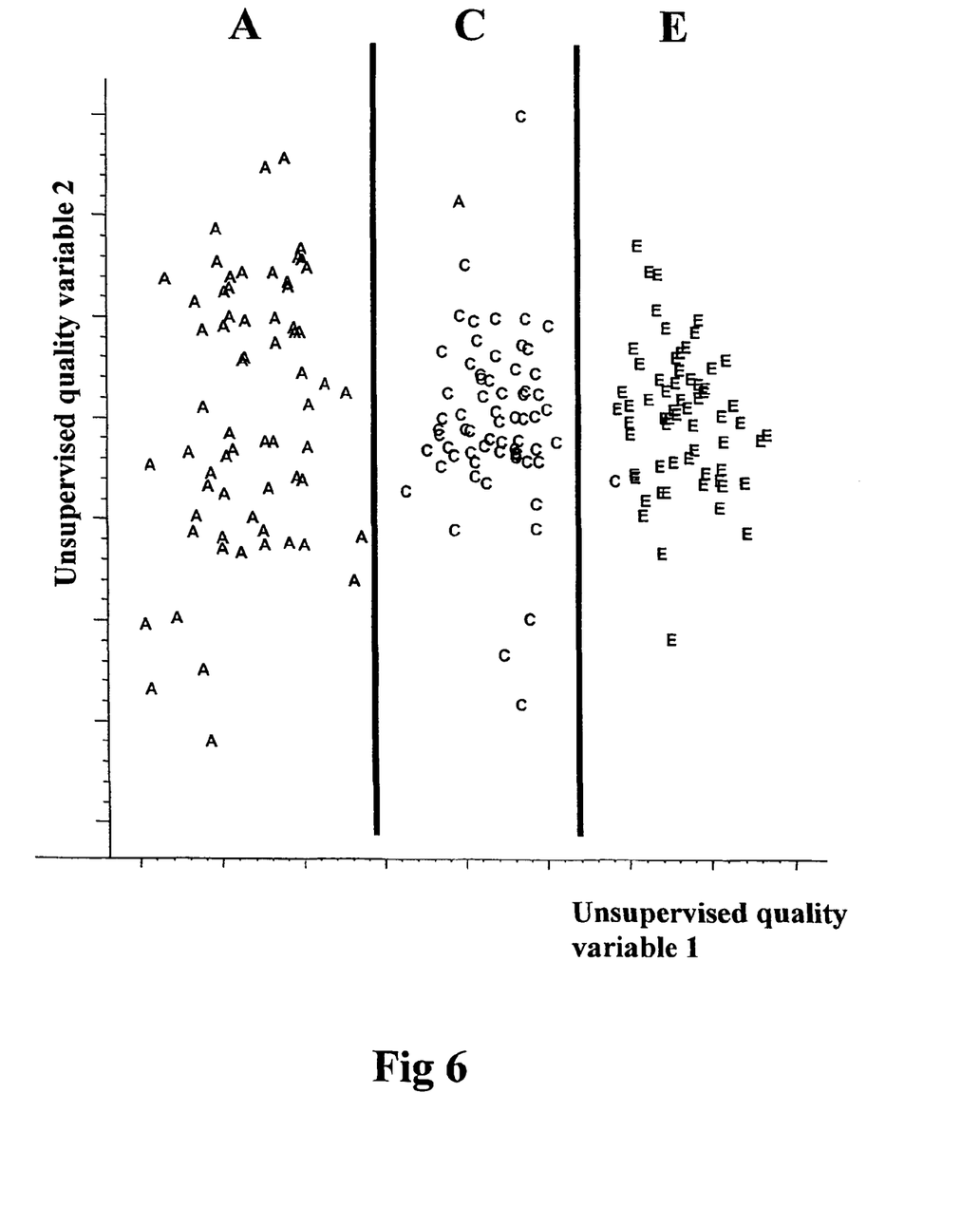
FIG. 6 shows the results of a classification of popcorn berries, a Principal Component Analysis of the three classes (A, C, and E) obtained after sorting according to the inventive method.

Sorting was performed by using a larger sample of the same batch of popcorn, which was separated into 5 classes (A, B, C, D, and E), each class being collected in a container. Samples from classes A, C, and E were tested for popping performance and also analyzed as described above. A Principal Component Analysis of the spectra in class A, C, and E, respectively, are shown in FIG. 6.

In a microwave popping test all berries in class C popped properly. However, only 1 berry out of 6 from class A and 1 berry out of 8 from class E, on average, resulted in a popcorn, i.e. the main part of the berries in these classes remained non-popped.

A class, which is more homogeneous in popping performance, could thus be obtained by sorting according to the inventive method.

The invention claimed is:

1. A method of sorting granules within a bulk of granules, having an inherent variation, from a heterogeneous population by sorting from said bulk at least three classes of granules, having less variation than said inherent variation, which represents a quality of composition with reference to any organic material of said granules, wherein the method comprises the steps of:
   (a) distributing each of said granules to be sorted as a separate granule in a sorting device;
   (b) exposing said separate granule to energy from at least one energy source;
   (c) recording a first multivariate signal from at least one point of each separate granule by means of at least one sensor;
   (d) estimating a magnitude of a second signal, by means of a calibration model previously obtained by means of a multivariate calibration method previously performed on a subset of said population between said first multivariate signal and said quality of composition, the second signal estimating the magnitude of at least one quality variable of inherent, univariate variation; and
   (e) sorting said granules by said sorting device to at least three collected classes in dependence on the magnitude of said second signal;
   wherein said first multivariate signal is recorded for a time period of less than 5 ms, at any point of said separate granule.

2. Method as in claim 1, wherein before step (d) said first multivariate signal is transformed by means of a pretreatment.

3. Method as in claim 1, wherein said quality of composition is an undefined quality of composition.

4. Method as in claim 1, wherein said calibration method is based on an unsupervised multivariate method.

5. Method as in claim 1, wherein said quality of composition is a defined quality of composition.

6. Method as in claim 1, wherein calibration method is based on a supervised multivariate method.

7. Method as in claim 1, wherein said quality of composition is a chemical quality, a structural quality, a sensoric quality, or a functional quality, or a combination thereof.

8. Method as in claim 1, wherein said emitted energy is electromagnetic radiation or sonic waves.

9. Method as in claim 8, wherein said electromagnetic radiation or sonic waves is ultraviolet light, visual light, near infrared light, infrared light, fluorescent light, ultrasonic waves, microwaves, or nuclear magnetic resonance, or a combination thereof.

10. Method as in claim 1, wherein said first multivariate signal is recorded as transmitted, reflected, or emitted energy.

11. A method for sorting a heterogeneous population of granules, the method comprising:
    (a) distributing each granule as an individual granule in a sorting device;
    (b) exposing each individual granule to energy from at least one energy source;
    (c) recording a first multivariate signal with at least one sensor, from at least one point on each granule, wherein said first multivariate signal is recorded for a time period of less than 5 ms, at any point of said separate granule;
    (d) predicting a second signal for each granule from the first multivariate signal of each granule and at least one quality of composition of the population of granules, wherein said second signal expresses the magnitude of at least one quality variable of inherent univariate variation, said prediction being obtained by means of a multivariate calibration method previously performed on a subset of said population between said first multivariate signal and said quality of composition; and
    (e) separating each granule into at least one collected class by said sorting device;
    wherein each granule is separated in dependence on the magnitude of the second signal of each granule;
    wherein the collected class is more homogeneous than the heterogeneous population of granules.

12. Method as in claim 11, wherein the granules are agricultural products.

13. Method as in claim 12, wherein the agricultural products are grains, seeds, kernels, popcorn, wheat, or cocoa beans.

14. Method as in claim 11, wherein before step (d) said first multivariate signal is transformed by means of a pretreatment.

15. Method as in claim 11, wherein said quality of composition is an undefined quality of composition.

16. Method as in claim 11, wherein said calibration method is based on an unsupervised multivariate method.

17. Method as in claim 11, wherein said quality of composition is a defined quality of composition.

18. Method as in claim 11, wherein calibration method is based on a supervised multivariate method.

19. Method as in claim 11, wherein said quality of composition is a chemical quality, a structural quality, a sensoric quality, or a functional quality, or a combination thereof.

20. Method as in claim 11, wherein said emitted energy is electromagnetic radiation or sonic waves.

21. Method as in claim 20, wherein said electromagnetic radiation or sonic waves is ultraviolet light, visual light, near infrared light, infrared light, fluorescent light, ultrasonic waves, microwaves, or nuclear magnetic resonance, or a combination thereof.

22. The method of claim 11, wherein said first multivariate signal is recorded for a time period of less than 20–30 ms, at any point of said granule.

23. Method as in claim 11, wherein said first multivariate signal is recorded as transmitted, reflected, or emitted energy.

24. The method of claim 11, wherein before step (e) said first multivariate signal is transformed by a pretreatment.

25. Method as in claim 1, wherein the granules are agricultural products.

26. Method as in claim 25, wherein the agricultural products are grains, seeds, kernels, popcorn, wheat, or cocoa beans.

\* \* \* \* \*